United States Patent [19]

Herrmann et al.

[11] Patent Number: 5,481,045
[45] Date of Patent: Jan. 2, 1996

[54] SULFONATED 2,2'-BIS (DIPHENYLPHOSPHINOMETHYL)-1,1'-BINAPHTHALENES, PROCESS FOR THEIR PREPARATION AND THEIR USE IN A PROCESS FOR THE HYDROFORMYLATION OF OLEFINICALLY UNSATURATED COMPOUNDS

[75] Inventors: Wolfgang A. Herrmann, Giggenhausen; Rainer Manetsberger, München; Helmut Bahrmann, Hamminkeln; Christian Kohlpaintner, Stephanskirchen; Peter Lappe, Dinslaken, all of Germany

[73] Assignee: Hoechst Aktiengesellschaft, Germany

[21] Appl. No.: 240,902

[22] Filed: May 11, 1994

Related U.S. Application Data

[62] Division of Ser. No. 66,553, May 25, 1993, Pat. No. 5,347,045.

[30] Foreign Application Priority Data

May 29, 1992 [DE] Germany ............. 42 17 803.7
Dec. 28, 1992 [DE] Germany ............. 42 44 274.5

[51] Int. Cl.⁶ ..................... C07C 47/02; C07C 47/11
[52] U.S. Cl. .............................. 568/454; 568/444
[58] Field of Search ...................... 568/454, 444

[56] References Cited

U.S. PATENT DOCUMENTS 5,200,380  4/1993  Herrmann et al. ............. 502/166

Primary Examiner—Nicky Chan
Attorney, Agent, or Firm—Jordan B. Bierman; Bierman and Muserlian

[57] ABSTRACT

Sulfonated diphosphines of the formula

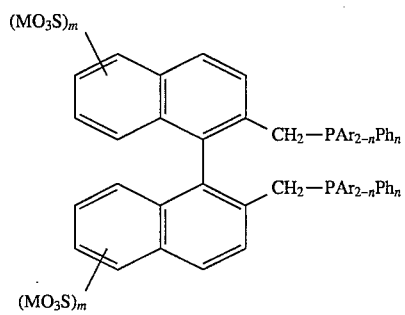

in which Ar is $m\text{-}C_6H_4\text{-}SO_3M$, M is hydrogen, ammonium, a monovalent metal, or the chemical equivalent of a polyvalent metal; Ph is phenyl; the m's are individually 1 or 2, and the n's are individually 0, 1, or 2. A method of their preparation and the hydroformylation of olefins and olefinically unsaturated compounds using these compounds as a constituent of water-soluble catalyst systems are also disclosed.

13 Claims, No Drawings

SULFONATED 2,2'-BIS (DIPHENYLPHOSPHINOMETHYL)-1,1'-BINAPHTHALENES, PROCESS FOR THEIR PREPARATION AND THEIR USE IN A PROCESS FOR THE HYDROFORMYLATION OF OLEFINICALLY UNSATURATED COMPOUNDS

This application is a division of application No. 08/066,553 filed May 25, 1993 now U.S. Pat. No. 5,347,065.

This Application claims the priorities of German Applications P 42 17 803.7, filed May 29, 1992 and P 42 44 274.5, filed Dec. 8, 1992.

The invention relates to novel sulfonated diphosphines and to their preparation. They form complex compounds with metals of Group VIII of the Periodic Table of the Elements (IUPAC version) and can be used as catalysts.

BACKGROUND OF THE INVENTION

Complex compounds containing a metal of Group VIII of the Periodic Table as the central atom and, as ligands, P(III) compounds such as phosphines or phosphites, and optionally other complexing groups, have recently become increasingly important as catalysts. Thus the reaction, extensively practiced in industry, of olefins with carbon monoxide and hydrogen to yield aldehydes (hydroformylation) is carried out in the presence of catalyst systems composed of rhodium and triphenylphosphine. Catalysts based on complex compounds containing phosphines have also proven successful for the reaction of methanol with synthesis gas to give higher alcohols, especially ethanol and propanol (homologization). In such cases, the ligands are usually present in excess, so that the catalyst system is composed of complex compound and free ligand. Since these systems are soluble in organic media, the reaction is carried out in a homogeneous phase.

The reaction can also be carried out in the heterogeneous phase. This process variant is particularly convenient because it provides a simple way of separating the water-dissolved catalyst from the water-insoluble reaction product under mild conditions. The hydroformylation process described in DE 26 27 354 C2, for example, works on this principle. The system rhodium/sodium triphenylphosphine trisulfonate is used as the catalyst.

In addition to monophosphines, diphosphines are also used as constituents of catalyst systems in which the other component is a metal of Group VIII of the Periodic Table. For example, DE-A 40 40 315 relates to the preparation of aldehydes by reaction of monoolefins, non-conjugated polyolefins, cycloolefins, or derivatives of these classes of compounds, with carbon monoxide and hydrogen in the presence of rhodium/diphosphine catalysts. Sulfonated 2,2'-bis-(diphenylphosphinomethyl)biphenyls or 2-(diphenylphosphinomethyl)- 1-[2-diphenylphosphinomethyl)phenyl]naphthalenes are used as the diphosphines in this process. Together with the rhodium, they provide catalysts which are distinguished from the known rhodium/monophosphine systems by increased activity.

SUMMARY OF THE INVENTION

The assumption that the composition of the product and the activity of rhodium complex catalysts depend on the chemical characteristics of the ligands creates an opportunity to develop novel ligands. This opens up the possibility of varying the course of the reaction so that particular products are formed preferentially or—in some cases—even exclusively. It is further required that the ligands and the complex compounds formed therefrom are soluble in water so as to benefit from the above-described advantages of hydroformylation in a two-phase system.

DETAILED DESCRIPTION OF THE INVENTION

The invention relates to novel sulfonated 2,2'-bis(diphenylphosphinomethyl)- 1,1'-binaphthalenes of the formula

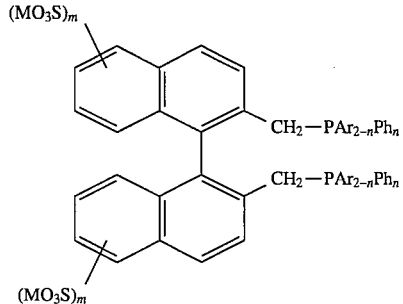

wherein Ar is $m\text{-}C_6H_4\text{-}SO_3$ M, M is hydrogen, ammonium, a monovalent metal or the chemical equivalent of a polyvalent metal; Ph is phenyl; the m's individually are 1 or 2 and the n's are individually 0, 1, or 2.

The parent substance used for the preparation of the novel compounds is 2,2'-bis(diphenylphosphinomethyl)-1,1'-binaphthalene. This compound is obtained in a multistep synthesis by (1) reductive dimerization of 1-bromo-2-methylnaphthalene with magnesium to give 2,2'-dimethyl-1,1'-binaphthalene, (2) reaction of the binaphthalene with butyl lithium to give the dilithium compound, and (3) reaction of the dilithium compound with chlorodiphenylphosphine. Instead of reacting 2,2'-dimethyl-1,1'-binaphthalene with butyl lithium, it is also possible to convert it to 2,2'-bis(bromomethyl)-1,1'-binaphthalene with N-bromosuccinimide. Reaction of the dibromo compound with diphenyl phosphinate gives 2,2'-bis(diphenylphosphinylmethyl)- 1,1'-binaphthalene, which is reduced with trichlorosilane to give 2,2'-bis(diphosphinomethyl)-1,1'-binaphthalene. To introduce sulfonic acid groups into the binaphthyl radical and into the phenyl radicals, the diphosphine is treated with excess sulfur trioxide in the form of oleum as the sulfonating agent.

Of importance for the degree of sulfonation which can be achieved are the $SO_3$ concentration in the oleum, the reaction temperature, and the reaction time. These parameters are interrelated and influence each other.

It has proven successful to use oleum containing at least 10% to 65% by weight of sulfur trioxide. The sulfonating agent is used in excess, based on the diphosphine. It is convenient to use 25 to 80, preferably 40 to 70, mol of $SO_3$ per mol of 2,2'-bis-(diphenylphosphinomethyl)- 1,1'-binaphthalene. Oleum having a high concentration of free $SO_3$, i.e. a proportion of at least about 40% to 65% by weight, gives products which contain at least four $SO_3H$ groups and, therefore, have excellent water solubility. Concentrations of free $SO_3$ in oleum which are lower than about 40% by weight give products with a lesser degree of sulfonation, i.e. diphosphines which have only a limited water solubility.

The reaction temperature is 0° to 25° C., preferably 0° to 10° C. In principle, it is also possible to use higher temperatures, but these promote the oxidation of the diphosphines to phosphine oxides appreciably more than the sulfonation, so that the overall yield of sulfonated phosphines decreases. Therefore, it is not recommended to compensate for low concentrations of free $SO_3$ by raising the reaction temperature. On the other hand, it is possible to influence the degree of sulfonation of the diphosphine by means of the reaction time. Longer reaction times give compounds with a higher degree of sulfonation than shorter reaction times. In general, the reaction requires 10 to 60 and preferably 15 to 48 hours in the above temperature ranges. These times apply especially when using oleum which contains about 40% by weight or more of free oleum. Less concentrated oleum leads only to partially sulfonated compounds, even with long reaction times; furthermore, increase in the formation of oxidation products cannot be fully avoided. It is therefore convenient to carry out the sulfonation with more highly concentrated oleum and to control the degree of sulfonation by means of the reaction time.

Concentrated sulfuric acid has proven successful as a solvent for the starting compound to be sulfonated, namely, 2,2'-bis(diphenylphosphinomethyl)- 1,1'-binaphthalene. This solution can be introduced into oleum in portions or oleum can be added thereto portionwise. It is recommended that the reaction mixture be stirred vigorously and thoroughly cooled; the reactants should be brought together slowly and in small portions so that the heat of reaction can be dissipated without difficulty. By this means, rather than the sulfonation proceeding in an uncontrolled manner, $SO_3H$ groups are introduced successively into the binaphthyl and phenyl radicals. Furthermore, oxidation of the phosphorus compound is effectively prevented. After all the sulfonating agent or diphosphine has been added, the afterreaction can take place at room temperature, i.e. at about 20° to 25° C., and essentially without external cooling. It is convenient, however, to stir the reaction mixture at this stage as well, so that any heat of reaction still being produced is uniformly distributed and can be dissipated without delay.

Following the sulfonation, the reaction solution is hydrolyzed. In this process step, care should be taken to insure that the temperature does not exceed about 30° C.; moreover, it is advantageous to maintain the temperature at 15° to 25° C. It is therefore recommended that the reaction+mixture be carefully added to ice or hydrolyzed with ice or ice-water with provision for intensive external cooling. The dilute solution, containing essentially sulfuric acid and 2,2'-bis-(diphenylphosphinomethyl)- 1,1'-binaphthalene with different degrees of sulfonation, is worked up in a further process step.

To do this, the solution containing sulfuric acid is neutralized with an alkaline reagent such as an alkali metal hydroxide or alkali metal carbonate, preferably sodium hydroxide. In order to maintain the volume of the reaction mixture as low as possible and to precipitate a substantial part of the alkali metal sulfate formed, the neutralizing agent is used as a highly concentrated solution or in undissolved solid form, e.g. flakes or pellets of caustic soda.

Because of its reduced solubility at lower temperatures, the bulk of the alkali metal sulfate can be removed from the solution by cooling. The appropriate temperatures depend on the concentration of the sulfate in the solution and the temperature profile of its solubility. The most favorable conditions therefore have to be determined by experiments in each individual case. The sulfate can be separated off in one step or in several steps; it has proven convenient to carry out the crystallization in two steps.

After separation of the alkali metal sulfate, the solution is concentrated to dryness, preferably under an oil-pump vacuum, and the diphosphines with different degrees of sulfonation are extracted from the crystal slurry in the form of their alkali metal salts. Suitable extractants include mixtures of lower alcohols (i.e. alcohols having up to 5 carbon atoms in the molecule, such as methanol, ethanol or propanol) with water. The extraction is carried out by conventional methods in one or more steps, preferably two to four steps. The extracts are combined and concentrated to dryness.

It has also proven successful to react the solution containing sulfuric acid with a mixture of a water-insoluble amine and an organic solvent and to extract the sulfonates as amine salts. Suitable amines are those having 10 to 60—preferably 13 to 36—carbon atoms, e.g. methyldioctylamine, tri-n-octylamine, triisooctylamine, tri-2-ethylhexylamine, and tridodecylamine, preferably triisooctylamine. Aliphatic and aromatic hydrocarbons or hydrocarbon mixtures, e.g. toluene or kerosene-like mixtures, especially toluene, are successfully used as organic solvents.

0.5 to 1.5 mol, preferably 0.8 to 1.2 mol, of amine is used per sulfonic acid equivalent. After vigorous mixing of the solution containing sulfuric acid and the amine solution, the aqueous and organic phases are separated from one another. The organic phase, containing the amine salt, is reacted with an aqueous solution of a base, the sulfonic acid salt of which is to be prepared. Examples of particularly suitable bases are sodium hydroxide and potassium hydroxide. This procedure gives an aqueous solution from which the desired sulfonic acid salt can be isolated.

Instead of the aqueous solution of the base being added all at once to the solution of the amine salt in the organic medium, it can also be added in portions. Such a gradual treatment of the amine solution, e.g. by adjusting the pH to certain values or ranges of values with the aid of the base, enables substantial separation of phosphine oxides from the sulfonation mixture and partial decomposition of the latter into products with different degrees of sulfonation.

The novel sulfonated diphosphines are colorless solids. Depending on the sulfonation conditions, they contain up to six sulfonic acid groups. The alkali metal salts are soluble in water and the solubility increases with the degree of sulfonation.

The free acids can be prepared by treating aqueous alkali metal salt solutions of the sulfonated diphosphine with a cation exchanger of the $H^+$ form. Other salts of the novel sulfonated diphosphines can be obtained from the acids by reaction with hydroxides, carbonates, ammonia, or amines.

The novel compounds have proven successful as components of catalyst system containing metals of Group VIII of the Periodic Table. In combination with rhodium, they are used especially as hydroformylation catalysts. Accordingly, the invention further relates to a process for the preparation of aldehydes by reaction of monoolefins, nonconjugated polyolefins, cycloolefins, or derivatives of these classes of compounds, with carbon monoxide and hydrogen at temperatures of 20° to 150° C. and pressures of 0.1 to 20 MPa in the presence of catalysts composed of water-soluble compounds of rhodium complexed with phosphines. The water-soluble phosphines used in the process are the above-described sulfonated 2,2'-bis-(diphenylphosphinomethyl)-1, 1'-binaphthyls.

The water-soluble rhodium/diphosphine complex compounds used as catalysts in the novel process are distinguished by a remarkably high activity, determined by the two criteria "activity" A and "productivity" P:

$$A = \frac{\text{mol of aldehyde}}{\text{mol of Rh} \times \text{min}}$$

-continued $$P = \frac{\text{g of aldehyde}}{\text{ml of catalyst solution} \times \text{hour}}$$

The values of these two parameters achieved with the processes of the state of the art are far exceeded by the procedure according to the invention. The formation of normal aldehydes is greater and the amounts of noble metal and phosphine discharged with the reaction product are smaller than in the known processes. Moreover, these results are obtained with a catalyst which has a distinctly smaller ligand/rhodium ratio than the catalysts used hitherto. These and other results of very great value for carrying out the process on the industrial scale could not be deduced from theoretical considerations nor predicted from practical experience.

It is not necessary to use the sulfonated diphosphines as pure compounds. It is also possible to use diphosphines with different degrees of sulfonation and/or sulfonate mixtures with different cations.

It has proven successful not to use rhodium and the diphosphines according to the invention in stoichiometric ratios, i.e. in accordance with the chemical composition of the rhodium complex compound which forms in the course of the hydroformylation reaction, but to use the dipbosphines in excess. The ratio of rhodium to diphosphine can thereby be varied within wide limits and about 1 to 130 mol of diphosphine can be used per mole of rhodium. The preferred molar ratio of rhodium to diphosphine is in the range from 1:2 to 1:25 and especially 1:2 to 1:10.

Rhodium is used as the metal or as a compound thereof. As the metal, it is finely divided or is precipitated in a thin layer on a support such as activated charcoal, calcium carbonate, aluminum silicate, or clay. The rhodium compounds are substances which are water-soluble or which become water-soluble under the reaction conditions. Suitable compounds are the various rhodium oxides, rhodium salts of inorganic hydro acids or oxy acids, and rhodium salts of aliphatic monocarboxylic or polycarboxylic acids. Examples are rhodium nitrate, rhodium sulfate, rhodium acetate, rhodium 2-ethylhexanoate, and rhodium malonate. Rhodium halide compounds, on the other hand, are less useful because of the lower activity of the resulting complexes and the corrosive behavior of the halide ions. It is further possible to use rhodium carbonyl compounds such as $Rh_3(CO)_{12}$ or $Rh_6(CO)_{16}$, or complex salts of rhodium, e.g. cyclooctadienylrhodium compounds. Rhodium oxide and especially rhodium acetate and rhodium 2-ethylhexanoate are preferred. It can be assumed that water-soluble rhodium complex compounds containing carbon monoxide and diphosphine as ligands are formed in the presence of synthesis gas under the conditions of the hydroformylation reaction. Together with the excess diphosphine dissolved in the water, they make up the catalyst system.

The catalyst solution is prepared from the components either in the hydroformylation reactor, or beforehand in a separate apparatus and then introduced into the hydroformylation reactor. The concentration of rhodium in the aqueous catalyst solution is 10 to 500 ppm by weight (based on the solution), preferably 10 to 100 ppm by weight, and especially 15 to 50 ppm by weight. The reaction temperature is between about 20° and 150° C., preferably 80° to 140° C., and especially 100° to 125° C.

The reaction of the olefin with carbon monoxide and hydrogen takes place at pressures of about 0,1 to about 30 MPa, preferably 1 to 12 MPa, and especially 1 to 5 MPa. The composition of the synthesis gas, i.e. the volume ratio of carbon monoxide to hydrogen, can extend over a wide range and can be varied, for example, between 1:10 and 10:1. In general, gas mixtures are used in which the volume ratio of carbon monoxide to hydrogen is about 1:1 or only a slight variation from this value in either direction.

The reaction of the reactants present in the liquid and gas phases takes place in Conventional reactors. The course of the reaction can be influenced by the fact that the aqueous catalyst solution must be saturated with the liquid or gaseous hydrophobic olefin and the synthesis gas. It is therefore necessary to create the largest possible contact areas between the phases. A procedure which has proven successful is to vigorously stir the liquid reactor contents (catalyst solution, optionally liquid olefin, and reaction product) and introduce the gaseous reactants (synthesis gas and optionally olefin) into the liquid phase via distributing devices. A procedure which has proven very successful is to keep the proportion of organic phase in the reaction mixture small. Surprisingly, the organic phase does not contribute to the solubility of the reactants in the aqueous phase and the reaction product is prevented from undergoing undesirable secondary reactions which cannot be excluded when the residence time of the product in the reactor increases. Accordingly, the volume ratio of aqueous to organic phase is adjusted to from 1:1 to 100:1, preferably 10:1 to 100:1. This can be done by continuously withdrawing an appropriate fraction of the reaction mixture from the reactor, separating the aqueous and organic phases from one another and recycling the aqueous phase into the reactor. The reaction can be carried out batchwise or, preferably, continuously.

The process according to the invention can be successfully applied to the reaction of monoolefins, non-conjugated polyolefins, cyclic olefins, and derivatives of these unsaturated compounds. The olefins used are not subject to any restrictions as far as molecular size is concerned. The olefinically unsaturated compounds can be linear or branched, and the double bonds can be within or at the end of the chains. Examples of olefins which can be used in the novel process are ethylene, propylene, butene-1, butene-2, pentene-1, 2-methylbutene-1, hexene-1, hexene-2, heptene-1, octene-1, octene-3, 3-ethylhexene-1, decene-1, undecene-3, 4,4-dimethyl nonene-1, dicyclopentadiene, vinylcyclohexene, cyclooctadiene, and styrene. Derivatives of these olefins which can be hydroformylated by the claimed procedure are e.g. alcohols, aldehydes, carboxylic acids, esters, nitriles, and halogen compounds, such as allyl alcohol, acrolein, methacrolein, crotonaldehyde, methyl acrylate, ethyl crotonate, diethyl fumarate, diethyl maleate, and acrylonitrile. The process is used with particular success for the hydroformylation of olefins and olefin derivatives having 2 to 20 and especially 2 to 8 carbon, atoms.

The following examples describe the preparation and properties of the novel compounds (Examples 1 to 10) and their use as constituents of catalysts for the hydroformylation of olefinically unsaturated compounds (Examples 11 to 16).

EXAMPLE 1

10.11 g (15.54 mmol) of 2,2'-bis(diphenylphosphinomethyl)-1,1'-binaphthalene is dissolved in 25 ml of concentrated sulfuric acid at room temperature. The solution is cooled to 0° C. and 50 ml of 65% oleum are added dropwise, the temperature being kept at a maximum of 10° C. The mixture is subsequently stirred for 48 hours. Hydrolysis and neutralization are carried out under conditions such that the temperature does not exceed 25° C. The precipitated sodium sulfate is filtered off and the filtrate is stirred into methanol.

The resulting white solid is separated off and the filtrate is concentrated to dryness. The residue is taken up in just enough water for complete dissolution and the aqueous solution is sprayed into twice the volume of methanol. The suspension obtained is filtered and the filtrate is concentrated to dryness. The combined filtrates are analyzed.

Characterization:

Solubility: 1300 g/l of water

Elemental analysis: 13.8% by weight of sulfur; 4.42% by weight of phosphorus; 9.9% by weight of sodium. The following molar ratios are calculated therefrom:

P:S=1:3; P:Na=1:3; S:Na=1:1, corresponding to the introduction of six $SO_3H$ groups into the 2,2'-bis(diphenylphosphinomethyl)-1,1'binaphthalene molecule $^{31}$P NMR:$\check{S}$=−9.0

This compound is called below BINAS.

EXAMPLE 2

The sulfonation of 2,2'-bis(diphenylphosphinomethyl)-1,1'-binaphthalene is carried out according to Example 1 and the progress of the reaction is followed by NMR spectroscopy of the solution containing sulfuric acid. The following measured values are obtained:

$^{31}$P NMR: δ=−9.0 (hexasulfonated)

δ=−9.89 (pentasulfonated)

δ=−12.03 (tetrasulfonated)

EXAMPLES 3–10

The sulfonation of 2,2'-bis(diphenylphosphinomethyl)-1,1'-binaphthalene is carried out according to Example 1, except that temperature, time, and $SO_3$ concentration are varied. The results are collated in the table below. Examples 5, 6 and 7 are comparative, in which higher reaction temperatures were used.

| Example | $SO_3$ content [% by weight] of the oleum | Reaction time [h] | Temperature [°C.] | Oxide formation [%][a] |
|---|---|---|---|---|
| 3 | 20 | 18 | 20 | 5 |
| 4 | 20 | 48 | 20 | 10 |
| 5 | 20 | 48 | 30 | 18 |
| 6 | 20 | 48 | 40 | 52 |
| 7 | 20 | 48 | 50 | 100 |
| 8 | 40 | 48 | 20 | 8 |
| 9 | 65 | 17 | 20 | 5 |
| 10 | 65 | 48 | 20 | 10 |

[a] previous standardization with completely oxidized, hexasulfonated 2,2'-bis(diphenylphosphinomethyl)-1,1'-binaphthalene

EXAMPLE 11

60.7 g (93.2 mmol) of 2,2'-bis(diphenylphosphinomethyl)-1,1'-binaphthalene is dissolved in 300 g of concentrated sulfuric acid at 0 to 10° C., 601.7 g of 65% oleum is added with the temperature being kept at 0° to 10° C., and the mixture is then stirred for 48 hours at room temperature. For hydrolysis, the sulfonation mixture is added dropwise to 3879.2 g of water over 30 min at temperatures below 10° C.

The sulfonation product is separated from the aqueous phase by extraction for 1 hour at 40° C. with a solution of 237.4 g of triisooctylamine in 948.8 g of toluene. The organic phase (1307.8 g) is then extracted at 40° C. with 3% by weight sodium hydroxide solution.

Up to a pH of 3.5, the aqueous phase (357.6 g) contains 16.8 mmol of P(III) and 2.6 mmol of P(V), based in each case on one kilogram of solution, and 3.8% of sulfate. In the pH range 3.5 to 4.8, the P(III) content of the aqueous phase (463.0 g) is 163 mmol and the P(V) content is 15.0 mmol, again based in each case on one kilogram of solution, and the sulfate content is 0.05%. In the range from pH 4.8 to pH 6.0, the useful product fraction (335.8 g) is separated off; it contains 212 mmol of P(III) and 1.0 mmol of P(V), based on one kilogram of solution.

EXAMPLES 12 to 17

Propylene and a $CO/H_2$ mixture made up of equal parts by volume are introduced into a 0.2 liter stainless steel autoclave, equipped with a stirrer, in an amount such that 10 liters/hour of off-gas can be withdrawn from the reactor. 300 ml per hour of aqueous catalyst solution (261 mg of Rh as the acetate and 13.9 mmol of P(III) in the form of BINAS, dissolved in 1000 ml of degassed water saturated with nitrogen) is simultaneously circulated through the reactor. The molar ratio of phosphorus to rhodium is 5.5:1, corresponding to a ligand/rhodium ratio of 2.75:1. The reactants are reacted at a pressure of 5 MPa. The remaining reaction parameters can be found in the Table.

In the Table, the results obtained with the process according to the invention (Examples 12 to 16) are compared with the result obtained with a procedure according to the state of the art [catalyst: rhodium/sodium triphenylphosphinetrisulfonate (TPPTS)] (Example 17). The experiments make it clear that, in the novel process, with a surprisingly low Rh/P ratio, a high catalyst activity is achieved and the n/i ratio is further increased. High conversions are obtained even when the olefin charge is considerably increased (Example 15).

While only a limited number of specific embodiments of the present invention have been expressly disclosed, it is, nonetheless, to be broadly construed and not to be limited except by the character of the claims appended hereto.

TABLE

|  | Example 12 | Example 13 | Example 14 | Example 15 | Example 16 | Example 17 (Comparative) |
|---|---|---|---|---|---|---|
| Experimental conditions | | | | | | |
| Catalyst | Rh/BINAS | Rh/BINAS | Rh/BINAS | Rh/BINAS | Rh/BINAS | Rh/TPPTS |
| Rhodium/ligand (mol/mol) | 1:2.75 | 1:2.75 | 1:2.75 | 1:2.75 | 1:2.75 | 1:100 |
| Temperature (°C.) | 110 | 116 | 122 | 122 | 128 | 122 |
| Pressure (MPa) | 5.0 | 5.0 | 5.0 | 5.0 | 5.0 | 5.0 |
| Propylene charge (g/h) | 40.0 | 40.0 | 40.0 | 129.0 | 40.0 | 40.0 |
| Experimental results | | | | | | |
| Conversion (%) | 44.7 | 40.4 | 50.8 | 47.9 | 57.8 | 39.0 |

TABLE-continued

|  | Example 12 | Example 13 | Example 14 | Example 15 | Example 16 | Example 17 (Comparative) |
|---|---|---|---|---|---|---|
| Activity | 43.92 | 42.81 | 55.48 | 163.3 | 61.41 | 15.11 |
| $\frac{\text{mol (n + i) aldehyde}}{\text{mol of Rh} \times \text{min}}$ | | | | | | |
| Productivity | 0.482 | 0.470 | 0.608 | 1.79 | 0.673 | 0.2 |
| $\frac{\text{g (n + i) of aldehyde}}{\text{ml of cat. sol.} \times \text{h}}$ | | | | | | |
| n/i ratio (parts by weight) | 97/3 | 97/3 | 97/3 | 98/2 | 97/3 | 93/7 |

What we claim is:

1. A process for the preparation of aldehydes comprising reacting compounds selected from the group consisting of monoolefins, nonconjugated polyolefins, cycloolefins, and derivatives thereof with carbon monoxide and hydrogen at a reaction temperature of 20° to 150° C. and a reaction pressure of 0.1 to 30 MPa in the presence of an aqueous catalyst solution composed of water soluble compounds of rhodium complexed with at least one sulfonated 2,2'-bis-(diphenylphosphinemethyl)- 1,1'-binaphthyl of the formula

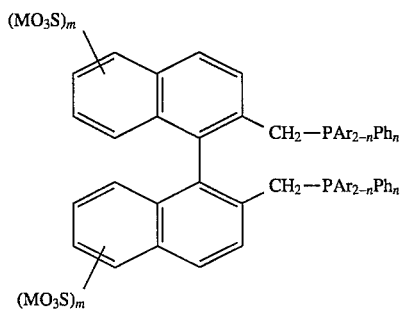

in which Ar is m-$C_6H_4$-$SO_3M$, M is selected from the group consisting of hydrogen, ammonium, a monovalent metal, and the chemical equivalent of a polyvalent metal, Ph is phenyl, the m's are individually 1 or 2, and the n's are individually 0, 1, or 2 wherein 1 to 130 tool of sulfonated diphosphines are used per mol of rhodium.

2. The process of claim 1 wherein 2 to 25 mol of sulfonated diphosphines are used per mol of rhodium.

3. The process of claim 2 wherein 2 to 10 mol of sulfonated diphosphines are used per mol of rhodium.

4. The process of claim 1 wherein there are 10 to 500 ppm by weight of rhodium in said aqueous catalyst solution, based on said solution.

5. The process of claim 4 wherein there are 10 to 100 ppm by weight of rhodium in said aqueous catalyst solution, based on said solution.

6. The process of claim 5 wherein there are 15 to 50 ppm by weight in said aqueous catalyst solution, based on said solution.

7. The process of claim 1 wherein said reaction temperature is 80° to 140° C.

8. The process of claim 7 wherein said reaction temperature is 100° to 125° C.

9. The process of claim 1 wherein said reaction pressure is 1 to 12 MPa.

10. The process of claim 9 wherein said reaction pressure is 1 to 5 MPa.

11. The process of claim 1 wherein said olefins or olefin derivatives have 2 to 40 carbon atoms.

12. The process of claim 11 wherein said olefins or olefin derivatives have 2 to 20 carbon atoms.

13. The process of claim 12 wherein said olefins or olefin derivatives have 2 to 8 carbon atoms.

* * * * *